United States Patent
Nielson et al.

(10) Patent No.: US 9,034,456 B2
(45) Date of Patent: May 19, 2015

(54) MEDICAL DEVICES AND METHODS OF MAKING THE SAME

(75) Inventors: Eric Nielson, Bellevue, WA (US); Dan VanCamp, Elk River, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1411 days.

(21) Appl. No.: 11/780,065

(22) Filed: Jul. 19, 2007

(65) Prior Publication Data

US 2008/0160259 A1 Jul. 3, 2008

Related U.S. Application Data

(60) Provisional application No. 60/877,571, filed on Dec. 28, 2006.

(51) Int. Cl.
| | |
|---|---|
| *B32B 5/16* | (2006.01) |
| *C22C 32/00* | (2006.01) |
| *A61F 2/91* | (2013.01) |
| *A61L 31/10* | (2006.01) |
| *A61L 31/12* | (2006.01) |
| *C25F 3/22* | (2006.01) |
| *A61F 2/00* | (2006.01) |

(52) U.S. Cl.
CPC ............... *C22C 32/00* (2013.01); *A61F 2/0077* (2013.01); *A61F 2/91* (2013.01); *A61L 31/10* (2013.01); *A61L 31/124* (2013.01); *C25F 3/22* (2013.01); *A61F 2230/0054* (2013.01)

(58) Field of Classification Search
None
See application file for complete search history.

(56) References Cited

U.S. PATENT DOCUMENTS

| | | | | |
|---|---|---|---|---|
| 3,926,567 | A | * 12/1975 | Fletcher et al. | ............... 428/403 |
| 4,365,356 | A | * 12/1982 | Broemer et al. | ........... 623/23.51 |
| 5,195,969 | A | 3/1993 | Wang et al. | |
| 5,270,086 | A | 12/1993 | Hamlin | |
| 5,366,504 | A | 11/1994 | Andersen et al. | |
| 5,637,113 | A | * 6/1997 | Tartaglia et al. | ............. 623/1.42 |
| 5,728,157 | A | * 3/1998 | Prescott | ........................ 523/113 |
| 5,780,807 | A | 7/1998 | Saunders | |
| 5,962,549 | A | * 10/1999 | Bonfield et al. | ............. 623/1.12 |
| 6,193,745 | B1 | * 2/2001 | Fogarty et al. | ............... 623/1.46 |
| 6,287,331 | B1 | 9/2001 | Heath | |
| 6,641,776 | B1 | * 11/2003 | Weaver et al. | ................. 264/642 |
| 6,726,712 | B1 | 4/2004 | Raeder-Devens et al. | |

(Continued)

FOREIGN PATENT DOCUMENTS

| | | |
|---|---|---|
| EP | 0 129 147 | 12/1985 |
| EP | 0222853 | 8/1990 |

(Continued)

OTHER PUBLICATIONS

Database WPI, Section Ch, Week 200149, Thomson Scientific, London, GB; Class D22, AN 2001-453758, XP002498990, "Composite Sintered compact for bone reinforcing material and dental implementation material, has surface layer contains smaller particles and protruding bigger particles of porous calcium phosphate compound".

(Continued)

*Primary Examiner* — Mark Ruthkosky
*Assistant Examiner* — Daniel J Schleis
(74) *Attorney, Agent, or Firm* — Seager, Tufte & Wickhem, LLC (57) ABSTRACT

Medical devices, such as, for example, endoprosthesis, and related methods are disclosed.

28 Claims, 5 Drawing Sheets

(56) References Cited

U.S. PATENT DOCUMENTS

| | | | |
|---|---|---|---|
| 7,604,662 B2 * | 10/2009 | Cambronne et al. | 623/1.46 |
| 2002/0144757 A1 | 10/2002 | Craig et al. | |
| 2003/0018380 A1 | 1/2003 | Craig et al. | |
| 2003/0049149 A1 * | 3/2003 | Landingham | 419/10 |
| 2003/0060873 A1 | 3/2003 | Gertner et al. | |
| 2003/0077200 A1 | 4/2003 | Craig et al. | |
| 2003/0206928 A1 * | 11/2003 | Tormala et al. | 424/400 |
| 2004/0044397 A1 | 3/2004 | Stinson | |
| 2004/0134886 A1 | 7/2004 | Wagner et al. | |
| 2004/0143317 A1 | 7/2004 | Stinson et al. | |
| 2005/0070990 A1 | 3/2005 | Stinson | |
| 2005/0123879 A1 * | 6/2005 | Andersson et al. | 433/174 |
| 2005/0131522 A1 | 6/2005 | Stinson et al. | |
| 2005/0192657 A1 | 9/2005 | Colen et al. | |
| 2005/0261760 A1 | 11/2005 | Weber | |
| 2006/0153729 A1 | 7/2006 | Stinson et al. | |
| 2006/0222844 A1 | 10/2006 | Stinson | |

FOREIGN PATENT DOCUMENTS

| | | |
|---|---|---|
| EP | 0 806 211 | 11/1997 |
| EP | 1 457 214 | 9/2004 |
| JP | 2001-098308 | 4/2001 |
| WO | WO86/06617 | 11/1986 |
| WO | 93/16656 | 9/1993 |
| WO | 2004/108021 | 12/2004 |
| WO | 2006/107677 | 10/2006 |

OTHER PUBLICATIONS

Schetsky, L. McDonald, "Shape Memory Alloys", Encyclopedia of Chemical Technology (3rd ed.), John Wiley & Sons, 1982, vol. 20, pp. 726-736.

Schetsky, L. "Shape Memory Alloys", Encyclopedia of Chemical Technology ($3^{rd}$ ed.), John Wiley & Sons, 1982, vol. 20, pp. 726-736.

U.S. Appl. No. 11/035,316, filed Jan. 3, 2005, Stinson et al.

U.S. Appl. No. 11/098,201, filed Apr. 4, 2005, Stinson.

* cited by examiner

MEDICAL DEVICES AND METHODS OF MAKING THE SAME

CROSS-REFERENCE TO RELATED APPLICATION

This application claims the benefit of the filing date of U.S. Provisional Patent Application Ser. No. 60/877,571, filed on Dec. 28, 2006, the entire contents of which are hereby incorporated by reference.

TECHNICAL FIELD

The invention relates to medical devices, such as, for example, endoprosthesis, and to related methods.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, a passageway can be reopened or reinforced, or even replaced, with a medical endoprosthesis. An endoprosthesis is typically a tubular member that is placed in a lumen in the body. Examples of endoprosthesis include stents, stent-grafts, and covered stents.

An endoprosthesis can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded (e.g., elastically or through a material phase transition). During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

SUMMARY

In one aspect, the invention features a medical device that has at least one portion including a composite material. The composite material includes a matrix and particles in the matrix that have a different chemical composition from the matrix. The particles protrude from a surface of the portion of the medical device by an average height of at least about 0.1 micron (e.g., 0.2 micron, 0.5 micron, one micron, two microns, three microns, four microns).

In another aspect, the invention features a method that includes forming a medical device from a composite material. The composite material includes a matrix and particles in the matrix that have a different chemical composition from the matrix. The medical device includes at least one portion, and the particles protrude from a surface of the portion by an average height of at least about 0.1 micron (e.g., 0.2 micron, 0.5 micron, one micron, two microns, three microns, four microns).

Embodiments can include one or more of the following features.

The particles can protrude from the surface of the portion of the medical device by an average height of at most about 20 microns.

The particles can have an average maximum dimension (e.g., an average diameter) of at least about 0.1 micron (e.g., at least about 0.2 micron, at least about 0.3 micron, at least about 0.4 micron, at least about 0.5 micron, at least about 0.6 micron, at least about 0.7 micron, at least about 0.8 micron, at least about 0.9 micron, at least about one micron) and/or at most about 40 microns (e.g., at most about 30 microns, at most about 20 microns, at most about 15 microns, at most about 10 microns, at most about nine microns, at most about eight microns, at most about seven microns, at most about six microns, at most about five microns, at most about four microns, at most about three microns, at most about two microns, at most about one micron).

The particles can include one or more metals, oxides, and/or alloys. In some embodiments, the particles can include a metal oxide, such as a refractory metal oxide. In certain embodiments, the particles can include an aluminum oxide (e.g., alumina), a niobium oxide, a titanium oxide (e.g., titania), a gallium oxide, and/or a chromic oxide. In some embodiments, the particles can include a non-metal oxide, such as an oxide of a metalloid. Examples of oxides of metalloids include silicon oxides (e.g., silica) and germanium oxides.

In certain embodiments, the particles can include platinum, palladium, rhodium, iridium, ruthenium, osmium, tungsten, tantalum, titanium, zirconium, hafnium, molybdenum, gold, copper, zinc, calcium, aluminum, nickel, and/or iron.

In some embodiments, the particles can include a carbide (e.g., silicon carbide, titanium carbide) and/or a nitride (e.g., silicon nitride, titanium nitride).

The particles can be elongated fibers.

The composite material can include at least about 0.5 percent by weight (e.g., at least about 0.8 percent by weight, at least about one percent by weight, at least about 1.2 percent by weight, at least about 1.4 percent by weight, at least about 1.6 percent by weight, at least about 1.8 percent by weight), and/or at most about two percent by weight (e.g., at most about 1.8 percent by weight, at most about 1.6 percent by weight, at most about 1.4 percent by weight, at most about 1.2 percent by weight, at most about one percent by weight, at most about 0.8 percent by weight) particles.

The matrix can include a metal (e.g., titanium) and/or an alloy (e.g., stainless steel, a platinum enhanced radiopaque stainless steel alloy, a cobalt-chromium alloy).

The matrix can define a depression or undercutting around at least one of the particles that protrudes from the surface of the portion of the medical device. The matrix defining the depression around at least one of the particles can undercut at least one of the particles, the at least one of the particles can protrude from the surface of the portion of the medical device.

The medical device can be an endoprosthesis, such as a stent.

The portion of the medical device can include a layer that includes the composite material. The medical device can include one portion including the composite material with one concentration of the particles, and another portion including the composite material with a different concentration of particles.

The medical device can include a coating that is disposed on the surface of the portion of the medical device. The coating can include a polymer.

The method can include forming a coating on the surface of the portion of the medical device. The method can include forming the composite material and/or annealing the composite material. In some embodiments, the method can include electropolishing and/or etching the medical device. In certain embodiments, the method can include treating (e.g., electropolishing) the medical device to increase the average height of the protrusion of the particles from the surface of the portion of the medical device.

In some embodiments, the method can include dissolving the particles to form pores in a portion of the medical device.

The method can include removing at least one of the particles that protrudes from the surface of the portion of the medical device. The method can include removing at least part of the matrix surrounding at least one of the particles that protrudes from the surface of the portion of the medical device.

Embodiments can include one or more of the following advantages.

In some embodiments, the medical device can exhibit enhanced retention of a coating, such as a polymer coating. For example, the particles that protrude from a surface of the medical device can engage can mechanically engage (e.g., interlock with) a polymer coating. In certain embodiments in which the particles provide enhanced retention of a coating on the medical device, the particles can also be relatively biocompatible.

In some embodiments, the medical device can have one or more properties that can be tailored and tuned. For example, the radiopacity and/or density of the composite material can be tailored so that the composite material has enhanced visibility under X-ray fluoroscopy and/or computed tomography (CT), while also having good biocompatibility and/or MRI compatibility. The mechanical properties of the composite material, such as stiffness and strength, can likewise be tailored and tuned. Different sections of the medical device can include composite materials that are similar but that have different properties (e.g., radiopacity, strength, stiffness). Such a medical device can be formed, for example, by varying the selections of materials in the composite material and/or by varying the concentrations of the materials. The composite material can be conveniently formable, for example, into tubing.

Other aspects, features, and advantages are in the description, drawings, and claims.

DETAILED DESCRIPTION

Figure 1A:
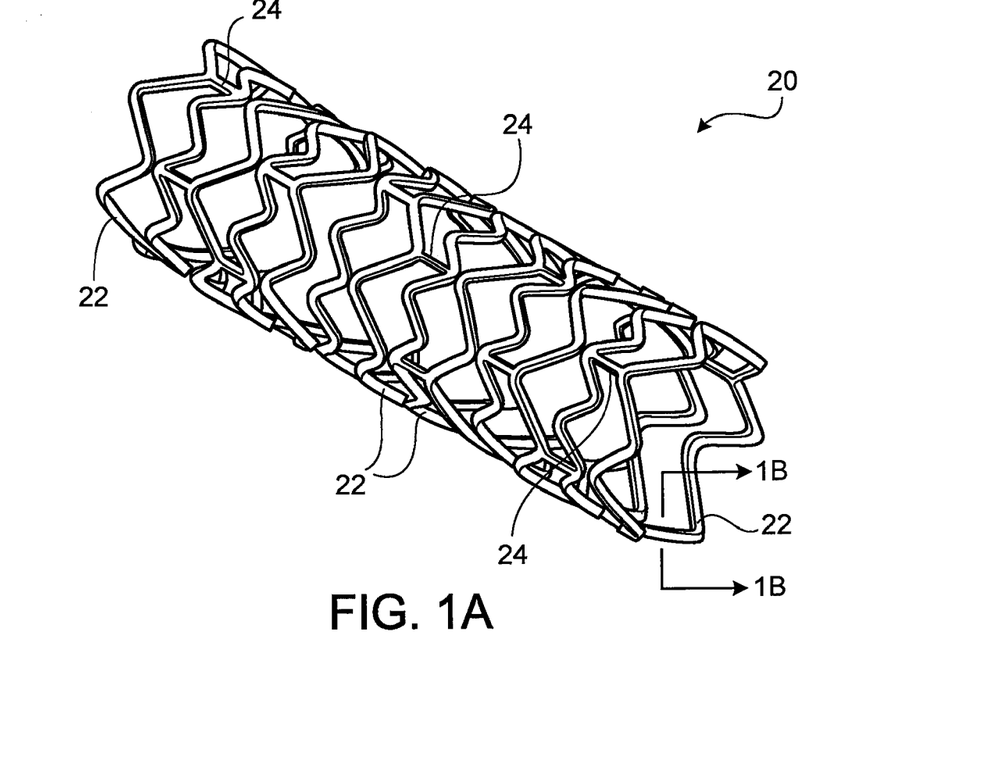
FIG. 1A is a perspective view of an embodiment of an expanded stent.

Referring to FIG. 1A, a stent 20 has the form of a tubular member defined by a plurality of bands 22 and a plurality of connectors 24 that extend between and connect adjacent bands 22. During use, bands 22 are expanded from an initial, small diameter to a larger diameter to contact stent 20 against a wall of a vessel, thereby maintaining the patency of the vessel. Connectors 24 provide stent 20 with flexibility and conformability that allow stent 20 to adapt to the contours of the vessel.

Figure 1B:
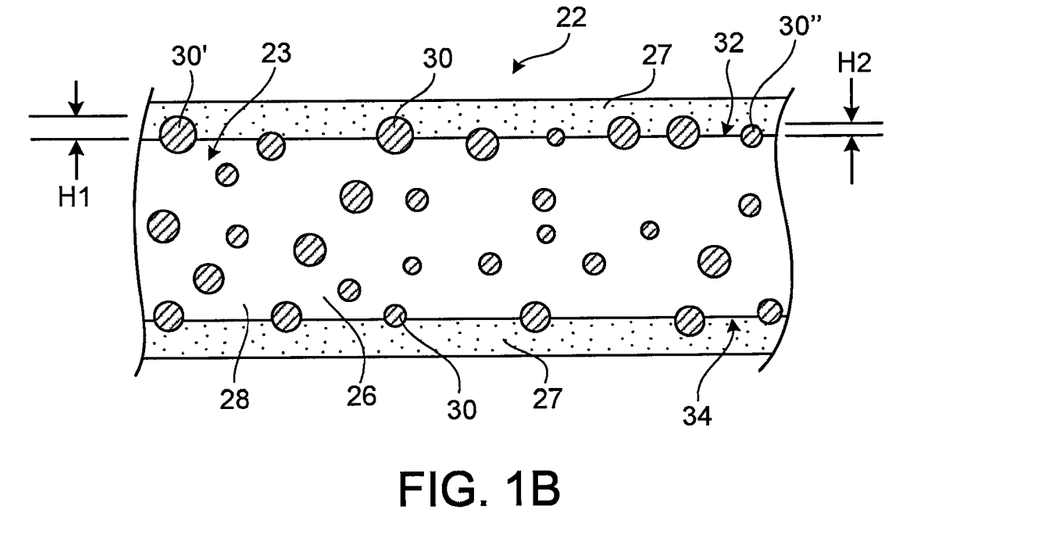
FIG. 1B is a cross-sectional view of a component of the stent of FIG. 1A, taken along line 1B-1B.

FIG. 1B shows a cross-sectional view of a band 22 of stent 20. As shown in FIG. 1B, band 22 includes a stent body portion 23 that is formed of a composite material 26, and a coating 27 over stent body portion 23. As used herein, a "composite material" is a material that includes (e.g., that is formed of) two or more intimately mixed, distinct constituent materials with different chemical compositions. Composite material 26 includes a metallic matrix 28 and a plurality of discrete particles 30. As used herein, a "matrix" is a continuous solid or porous material that partially and/or fully encloses or embeds one or more other materials (e.g., particles).

Stent body portion 23 of band 22 has an interior surface 32 and an exterior surface 34. Some of particles 30 protrude from interior surface 32, and some of particles 30 protrude from exterior surface 34. Other particles 30 are embedded within matrix 28. As shown in FIG. 1B, coating 27 is disposed on both interior surface 32 and exterior surface 34 of stent body portion 23. Particles 30 that protrude from interior surface 32 or exterior surface 34 help to retain coating 27 on stent body portion 23.

As shown in FIG. 1B, the particles that protrude from interior surface 32 and exterior surface 34 protrude by different heights. For example, particle 30' protrudes from surface 32 by a height H1, while particle 30" protrudes from surface 32 by a height H2 that is smaller than height H1. In some embodiments, particles 30 can protrude from interior surface 32 and/or exterior surface 34 by an average height of at least about 0.1 micron (e.g., at least about 0.5 micron, at most about 1.0 micron, at most about two microns, at most about three microns, at most about four microns) and/or at most about 20 microns (e.g., at most about 15 microns, at most about ten microns, at most at most about five microns). The average height by which particles protrude from a surface of a medical device or a portion of a medical device can be measured, for example, by using scanning electron microscopy (SEM) on a cross-section of the medical device or the portion of the medical device.

While FIG. 1B shows particles protruding from interior surface 32 and exterior surface 34 by different heights, in certain embodiments, particles can protrude from a surface of a stent body by substantially or approximately the same height (e.g., ≤5% difference).

Particles 30 can include, for example, one or more metals, oxides, and/or alloys.

Examples of metals include platinum, palladium, rhodium, iridium, ruthenium, osmium, tungsten, tantalum, titanium, zirconium, hafnium, molybdenum, gold, copper, zinc, calcium, aluminum, nickel, and iron.

Examples of oxides include metal oxides, such as refractory metal oxides. Examples of refractory metal oxides include titanium oxides (e.g., titania ($TiO_2$)), chromium oxides (e.g., chromic oxide ($Cr_2O_3$)), tungsten oxides, molybdenum oxides, niobium oxides, tantalum oxides, and rhenium oxides. In some embodiments in which a composite material includes a stainless steel matrix and chromium oxide particles, the composite material can be relatively resistant to corrosion. Additional examples of oxides include aluminum oxides (e.g., alumina ($Al_2O_3$)), silicon oxides (e.g., silica ($SiO_2$)), germanium oxides, and gallium oxides.

In some embodiments, the particles include metal oxides formed in situ within the stent material. For example, a metal particle can be incorporated into a stent material. The metal particle can then undergo oxidation to form metal oxides by scavenging oxygen from other metals in the stent material.

In some embodiments, particles 30 can include one or more ceramics. Examples of ceramics include alumina, zirconia ($ZrO_2$), silica, aluminum silicate ($Al_2SiO_5$), and magnesia (MgO). Additional examples of ceramics include carbides (e.g., silicon carbide, titanium carbide) and nitrides (e.g., silicon nitride, titanium nitride).

In certain embodiments, particles 30 can include graphite.

In some embodiments, particles 30 can include (e.g., can be formed of) one or more materials that are capable of providing stent 20 with tailored physical properties (e.g., density, radiopacity) and/or mechanical properties (e.g., strength).

As an example, particles 30 can be used to render stent 20 less radiopaque than a stent formed only of matrix 28. For example, a stent made of pure tantalum can have good biocompatibility and a low magnetic susceptibility that provides good visualization during magnetic resonance imaging (MRI). But in some embodiments, a pure tantalum stent may be too highly radiopaque, and as a result, visualization of the volume in the stent and of the tissue surrounding the stent during X-ray fluoroscopy and/or computed tomography (CT) may be obscured. To reduce the radiopacity, the stent can be made of a composite material including a tantalum matrix and particles of a less dense material, such as titanium. Since the titanium is less dense than tantalum, the radiopacity of a sample of the composite is reduced relative to an otherwise identical sample of tantalum. At the same time, since titanium has good biocompatibility and a low magnetic susceptibility, the composite also has good biocompatibility and MRI compatibility. Other high density materials, such as molybdenum, niobium, platinum, and their alloys, can be similarly modified as described above for tantalum. Reducing the radiopacity may be particularly beneficial for thick walled stents (e.g., peripheral vascular stents). In some embodiments, the presence of oxide particles on the surface can reduce eddy current and surface currents in MRI.

As another example, particles 30 can be used to render stent 20 more radiopaque than a stent formed only of matrix 28. For example, particles 30 can be formed of tantalum, and matrix 28 can be formed of titanium or a titanium alloy. Alternatively, particles 30 can be formed of nickel or tantalum, and matrix 28 can be formed of Nitinol. Increasing the radiopacity of stent 20 may be particularly beneficial in embodiments in which stent 20 is thin-walled, and may obviate the need for radiopaque markers on stent 20 in general.

Particles 30 can be formed using any of a number of different methods. In some embodiments, particles 30 can be formed using powder atomization. Other methods that can be used to form particles 30 include bubbling of molten material, sol-gel techniques, and precursor casting.

In some embodiments, particles 30 can enhance the mechanical properties of matrix 28. Without wishing to be bound by theory, it is believed that particles 30 can increase the stiffness (tensile modulus) and/or strength (yield strength) of matrix 28 by dispersion strengthening. For example, particles of tantalum, tungsten, and/or rhenium can increase the stiffness of a matrix including titanium or niobium. The enhanced mechanical properties may allow stent 20 to be formed with reduced wall thickness, without also compromising the performance of stent 20. A thinner walled stent may be more easily delivered through a tortuous path, may be implanted in a smaller body vessel, and/or may allow more fluid flow through the stent.

Matrix 28 can include (e.g., can be manufactured from) one or more biocompatible materials with mechanical properties that allow a stent including composite material 26 to be compacted, and subsequently expanded to support a vessel. In some embodiments, stent 20 can have an ultimate tensile yield strength (YS) of about 20-150 ksi, greater than about 15 percent elongation to failure, and a modulus of elasticity of about 10-60 msi. When stent 20 is expanded, the material can be stretched to strains on the order of about 0.3. Examples of materials that can be used in matrix 28 include metals and alloys. Examples of metals and alloys include stainless steel (e.g., 316L, BioDur® 108 (UNS S29108), 304L stainless steel); alloys including stainless steel and from five percent by weight to 60 percent by weight of one or more radiopaque elements such as platinum, iridium, gold, and/or tungsten (e.g., platinum enhanced radiopaque stainless steel (PERSS®) alloys), such as the alloys described in Craig et al., U.S. Patent Application Publication No. US 2003/0018380 A1, Craig et al., U.S. Patent Application Publication No. US 2002/0144757 A1, and Craig et al., U.S. Patent Application Publication No. US 2003/0077200 A1; Nitinol (a nickel-titanium alloy); cobalt alloys such as cobalt-chromium alloys (e.g., Elgiloy®); L605 alloys; MP35N; titanium; titanium alloys (e.g., Ti-6Al-4V, Ti-50Ta, Ti-10Ir); platinum; platinum alloys; niobium; niobium alloys (e.g., Nb-1Zr); Co-28Cr-6Mo; tantalum; tantalum alloys; chromium; and chromium alloys. Other examples of materials are described in Stinson, U.S. Patent Application Publication No. US 2005/0070990 A1, and Stinson et al., U.S. patent application Ser. No. 11/035,316, filed Jan. 3, 2005, and entitled "Medical Devices and Methods of Making The Same". Additional examples of materials include elastic biocompatible metals such as super-elastic or pseudo-elastic metal alloys, as described, for example, in Schetsky, L. McDonald, "Shape Memory Alloys", *Encyclopedia of Chemical Technology* (3rd ed.), John Wiley & Sons, 1982, vol. 20, pp. 726-736, and Stinson et al., U.S. Patent Application Publication No. US 2004/0143317 A1.

In some embodiments, matrix 28 can include one or more materials that enhance visibility by MRI (MRI-visible materials). Examples of MRI-visible materials include non-ferrous metals (e.g., copper, silver, platinum, gold) and non-ferrous metal-alloys containing paramagnetic elements (e.g., dysprosium, gadolinium) such as terbium-dysprosium, dysprosium, and gadolinium. Alternatively or additionally, matrix 28 can include one or more materials having low magnetic susceptibility to reduce magnetic susceptibility artifacts, which can interfere with imaging of tissue (e.g., adjacent to and/or surrounding stent 20). Low magnetic susceptibility materials include those described above, such as tantalum, platinum, titanium, niobium, copper, and alloys containing these elements.

Particles 30 can also include (e.g., be manufactured from) one or more biocompatible materials described above for matrix 28. Particles 30 can have the same compositions as each other, or can have different compositions from each other. The composition(s) of particles 30 can be different from the chemical composition(s) of matrix 28, and/or particles 30 and matrix 28 can have the same composition(s). In embodiments in which the particles have the same composition(s) as the matrix, deleterious metallurgical phases, such as those that can form along the interface between the particles and matrix, may be limited or prevented. For example, hollow particles, such as hollow tantalum spheres, can be incorporated within a tantalum matrix to lower the radiopacity of the tantalum matrix.

In embodiments in which particles 30 include one or more radiopaque materials to enhance radiopacity, particles 30 may include metallic elements having atomic numbers greater than 26 (e.g., greater than 43), and/or a density greater than about 9.9 g/cc. In certain embodiments, the radiopaque material can be relatively absorptive of X-rays. For example, the radiopaque material can have a linear attenuation coefficient of at least 25 $cm^{-1}$ (e.g., at least 50 $cm^{-1}$) at 100 keV. Examples of radiopaque materials include tantalum, platinum, iridium, palladium, hafnium, tungsten, gold, ruthenium, and rhenium. The radiopaque material can include an alloy, such as a binary, a ternary or more complex alloy, containing one or more elements listed above with one or more other elements such as iron, nickel, cobalt, or titanium. Examples of alloys including one or more radiopaque materials are described in Craig et al., U.S. Patent Application Publication No. US 2003/0018380 A1, Craig et al., U.S. Patent Application Publication No. US 2002/0144757 A1, and Craig et al., U.S. Patent Application Publication No. US 2003/0077200 A1.

Alternatively or additionally, particles 30 may include one or more MRI-visible materials. Examples of MRI-visible materials include oxide or carbide layers of dysprosium or gadolinium (e.g., $Dy_2O_3$, $Gd_2O_3$), superparamagnetic materials (e.g., $Fe_3O_4$, $CoFe_2O_4$, $MnFe_2O_4$, $MgFe_2O_4$), and transition metal oxides (e.g., oxides of iron, cobalt, and/or nickel).

The shape and size of particles 30 are not particularly limited. As shown in FIG. 1B, in some embodiments, particles 30 can be generally spherical in shape to provide isotropic performance, but in other embodiments, non-spherical shapes (e.g., fibers, plates, chards, prolated spheres) can alternatively or additionally be used. In some embodiments, particles 30 can have an average maximum dimension (e.g., an average diameter) of at least about 1 micron (e.g., at least about two microns, at least about three microns, at least about four microns, at least about five microns, at least about six microns, at least about seven microns, at least about eight microns, at most about nine microns, or at most about ten microns) and/or at most about 40 microns (e.g., at most about 30 microns, at most about 20 microns, at most about 18 microns, at most about 16 microns, at most about 14 microns, at most about 12 microns, at most about 10 microns, at most about nine microns, at most about eight microns, at most about seven microns, at most about six microns, at most about five microns, at most about four microns, at most about three microns, or at most about two microns).

In certain embodiments, such as when particles 30 are non-conductive (e.g., if particles 30 include a ceramic such as an oxide), the size of the particles can be relatively large. As described below, in some methods of making a stent, electropolishing is used to finish the stent. When non-conductive particles are included in the composite material, electropolishing may preferentially remove the matrix material, without affecting the non-conductive particles. As a result, depressions may form at the surface of the stent if enough matrix material is removed to liberate the particles, and/or the surface may include protruding non-conductive particles, both of which can cause the stent surface to be rough. This roughness can, for example, enhance the ability of the stent to retain a coating. By using relatively large non-conductive particles, the size of any depressions that are formed and/or the roughness caused by protruding non-conductive particles can be enhanced. In some embodiments, the maximum dimension of non-conductive particles can be at least about 0.1 micron (e.g., at least about 0.2 micron, at least about 0.5 micron, at least about 0.7 micron, at least about one micron) and/or at most about five microns (e.g., at most about four microns, at most about three microns, at most about two microns, at most about one micron).

Non-spherical particles (e.g., elongated fibers) can be randomly distributed within a matrix or preferentially oriented in a predetermined direction within the matrix to provide anisotropic performance. For example, fibers that are oriented circumferentially around a tubular member of a stent can enhance the hoop strength of the tubular member, which can help the stent to resist compression, thereby maintaining the patency of the body vessel. Fibers that are oriented radially can enhance the radial strength of the stent, and fibers that are oriented longitudinally (i.e., parallel to the length of the stent) can enhance axial stiffness. Magnetic non-spherical particles can be aligned by applying a magnetic field along a predetermined direction. Fibers can be formed having a first end heavier than a second end (e.g., by forming a stub on the first end and/or by tapering the size of the fiber). The fibers can then be placed into an unsolidified sheet of matrix material, in which the heavier ends of the fibers tend to align the fibers perpendicular to the longitudinal axis of the sheet. In some embodiments, asymmetrical fibers (e.g., those having one end heavier than another end) can be mixed with the matrix material and spin cast (e.g., about the longitudinal axis) in a mold to form a tubular member. The centrifugal force generated during spin casting can orient the fibers in the matrix material. For example, the fibers can orient radially, with the heavier ends outward of the lighter ends. Other methods of aligning fibers and making stents with aligned fibers are described, for example, in Stinson, U.S. Patent Application Publication No. US 2004/0044397. Within a composite material, particles 30 can have one or more shapes (e.g., spheres and fibers) and/or one or more sizes (e.g., a distribution of sizes).

Composite materials, matrices, and particles are described, for example, in Stinson, U.S. patent application Ser. No. 11/098,201, filed on Apr. 4, 2005, and entitled "Medical Devices Including Composites".

Coating 27 can be formed of, for example, one or more polymers. Examples of polymers include styrene-isobutylene-styrene block copolymers (SIBS); polycarboxylic acid; polyethylene oxide; polyphosphazenes; polyanhydrides (e.g., maleic anhydride polymers); poly(alpha-hydroxy acid)s, such as polylactic acid (PLA), polyglycolic acid (PGA), and copolymers and mixtures thereof (e.g., poly(L-lactic acid) (PLLA), poly(D,L-lactide), poly(lactic acid-co-glycolic acid), 50/50 (DL-lactide-co-glycolide)); stereopolymers of L- and D-lactic acid; poly(lactic acid)/poly(glycolic acid)/polyethyleneglycol copolymers; copolymers of polyurethane and poly(lactic acid); copolymers of α-amino acids; copolymers of α-amino acids and caproic acid; copolymers of α-benzyl glutamate and polyethylene glycol; copolymers of succinate and poly(glycols); polyphosphazene; polyhydroxy-alkanoates; copolymers of bis(p-carboxyphenoxy) propane acid and sebacic acid; sebacic acid copolymers; polyhydroxybutyrate and its copolymers; polypropylene fumarate; polydepsipeptides; polydioxanones; polyoxalates; poly(α-esters); polycaprolactones and copolymers and mixtures thereof (e.g., poly(D,L-lactide-co-caprolactone), polycaprolactone co-butylacrylate); polyhydroxybutyrate valerate and blends; polycarbonates (e.g., tyrosine-derived polycarbonates and acrylates, polyiminocarbonates, polydimethyltrimethyl-carbonates); polyglycosaminoglycans; macromolecules such as polysaccharides (e.g., hyaluronic acid, celluloses, hydroxypropylmethyl cellulose, gelatin, starches, dextrans, alginates, and derivates thereof); polypeptides; polygluconate; polylactic acid-polyethylene oxide copolymers; modified cellulose; poly(hydroxybutyrate); polybutylmethacrylate (PBMA); polyanhydrides (e.g., crystalline polyanhydrides, amorphous polyanhydrides); polyacetates; maleic anyhydride copolymers; polyorthoesters; polyphosphoester; poly-amino acids; polyamides; and mixtures and copolymers thereof.

Figure 2:
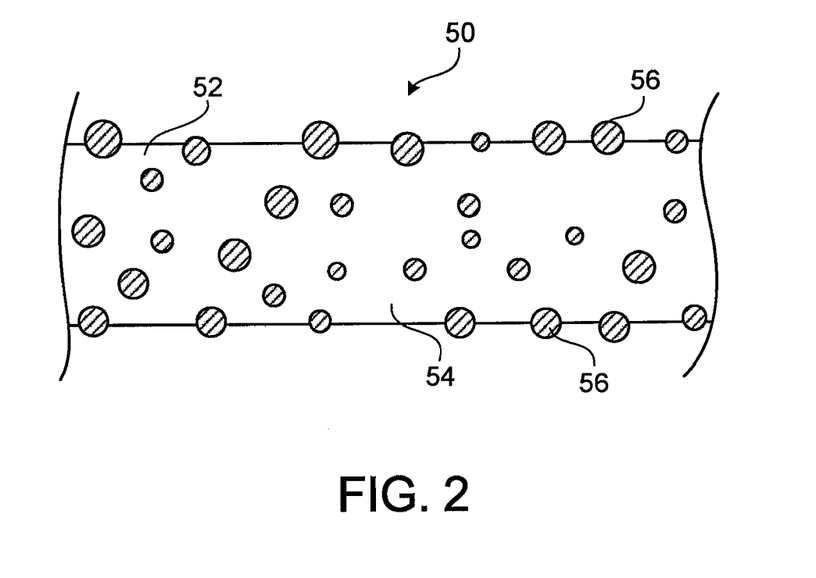
FIG. 2 is a cross-sectional view of an embodiment of a component of a stent.

While FIG. 1B shows a component of a stent (band 22) that is coated, in some embodiments, a stent can alternatively or additionally include one or more components that are not coated. For example, FIG. 2 shows a cross-sectional view of a component 50 (e.g., a band, a connector) of a stent that is formed of a composite material 52 including a metallic matrix 54 and particles 56 partially or fully embedded in matrix 54. Component 50 does not include a coating.

Figure 3:
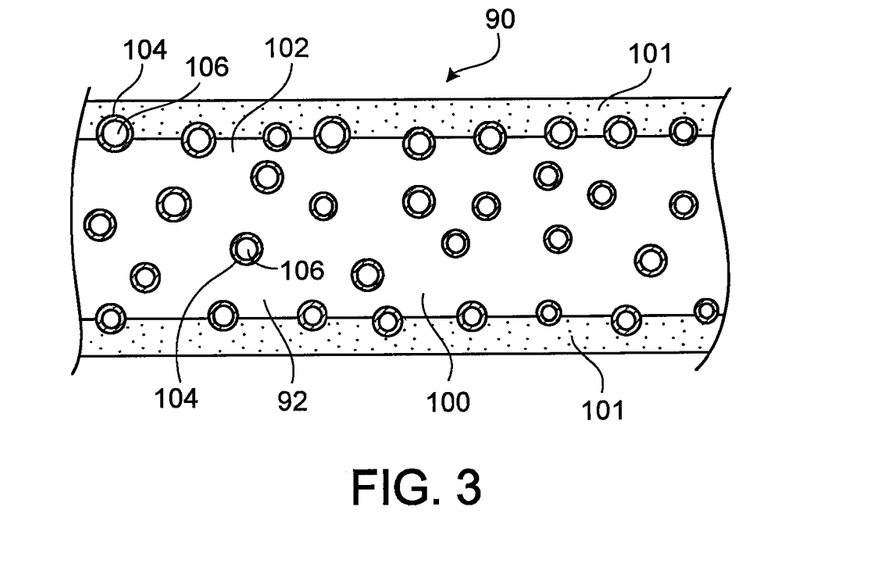
FIG. 3 is a cross-sectional view of an embodiment of a component of a stent.

The particles in a composite material can be solid (e.g., like particles 30) or hollow. For example, FIG. 3 shows a component 90 (e.g., a band, a connector) of a stent including a stent body portion 92 formed of a composite material 100, and a coating 101 over stent body portion 92. Composite material 100 includes a metallic matrix 102 and hollow particles 104 defining cavities 106. Hollow particles 104 can decrease the density of composite 100, while still providing, for example, strengthening effects. In some embodiments, cavities 106 can have an average diameter or width of at least about 0.1 micron (e.g., at least about 0.2 micron, at least about 0.4 micron, at least about 0.6 micron, at least about 0.8 micron, at least about one micron) and/or at most about five microns (e.g., at most about four microns, at most about three microns, at most about two microns, at most about one micron). The hollow particles in a composite material can have cavities of the same size and/or cavities of different sizes. Hollow particles can be made, for example, by using a puffing nozzle to blow bubbles from a flowing molten sheet of material, by using a concentric nozzle and a drop tower, by sol-gel methods, or by using precursor methods in which a sphere is formed within or around another material that is subsequently removed.

In some embodiments, a composite material can include both hollow particles and solid particles. The hollow particles can be smaller or larger than the solid particles. In certain embodiments, the hollow particles and the solid particles can be of the same or similar size. In some embodiments, a combination of sizes of particles can be used. Within a composite material, the particles can all be solid, can all be hollow, or can be a combination of hollow and solid particles.

In some embodiments, a composite material can include particles including a coating having a different chemical composition from the chemical composition of the particles and the matrix of the composite material. Certain coatings can be more compatible (e.g., miscible) with the matrix material than the particles, and can enhance incorporation of the particles into the matrix. The coating on the particles may act as a buffer layer or a protective layer between the particles and the matrix by including a material that combines well (e.g., alloys well) with the matrix material. This ability to combine well with the matrix material can, for example, reduce the likelihood of formation of deleterious phases. For example, the radiopacity of titanium can be increased by sputter coating tungsten spheres with tantalum, and adding the coated spheres into the titanium. The coating can be advantageous because tungsten and titanium can form undesirable intermetallic phases, such as omega, when they come into contact with each other.

The total concentration of particles in a composite material can vary. In some embodiments, a composite material can include at least about 0.5 percent by weight (e.g., at least about 0.8 percent by weight, at least about one percent by weight, at least about 1.2 percent by weight, at least about 1.4 percent by weight, at least about 1.6 percent by weight, at least about 1.8 percent by weight) and/or at most about two percent by weight (e.g., at most about 1.8 percent by weight, at most about 1.6 percent by weight, at most about 1.4 percent by weight, at most about 1.2 percent by weight, at most about one percent by weight, at most about 0.8 percent by weight) of particles. Multiple composite materials with different concentrations of particles, and/or different compositions of particles and/or matrix, can be used in a medical device. For example, for a stent formed of a composite material including a stainless steel matrix and tantalum particles, the end portions of the stent may have a higher concentration of tantalum than other portions of the stent. This can, for example, enhance contrast and visualization of the stent during fluoroscopy. As another example, the concentration of particles at the end portions of a stent can be selected to make the end portions more flexible, so that the end portions can flare out and secure the stent against a vessel. As an additional example, the concentration of particles at the middle portion of a stent can be selected to have a relatively low yield strength, so that the stent can be easily plastically deformed with little recoil during expansion of the stent.

The selections of materials for a metallic matrix and for the particles in the matrix can be guided by the desired properties of the composite material. For example, as discussed above, the radiopacity of a matrix can be increased or decreased by incorporating denser or less dense particles, respectively. Particles of one or more chemical compositions, sizes, types (e.g., solid or hollow), and/or shapes can be used to tailor and tune the desired properties. Other considerations for the selection of materials include the compatibility between the materials. For example, the materials for a matrix and for the particles in the matrix may be selected to be miscible and not to form undesirable metallurgical phases that are deleterious to engineering properties. The materials for the matrix and the particles may be selected so that their reduction potentials are relatively similar, thereby to reduce the occurrence of galvanic corrosion in the body. The melting points of the materials for the matrix and the particles may also be different (e.g., different by greater than about 50° C.), so that the particles do not melt if the matrix material is molten during fabrication of the composite material. In some embodiments, the melting points of the materials for the matrix and the particles may be somewhat compatible so that during fabrication (e.g., laser cutting described below) the composite material does not segregate, or one material does not substantially preferentially melt over another material. Particles 30 may be selected to have ductility similar to the matrix or at least high enough to deform during cold working of the matrix (e.g., during tube manufacturing) without fracturing. For example, titanium particles that have been annealed (softened) after quench atomization may be more likely to deform within a tantalum matrix than as-quenched particles.

Figure 4:
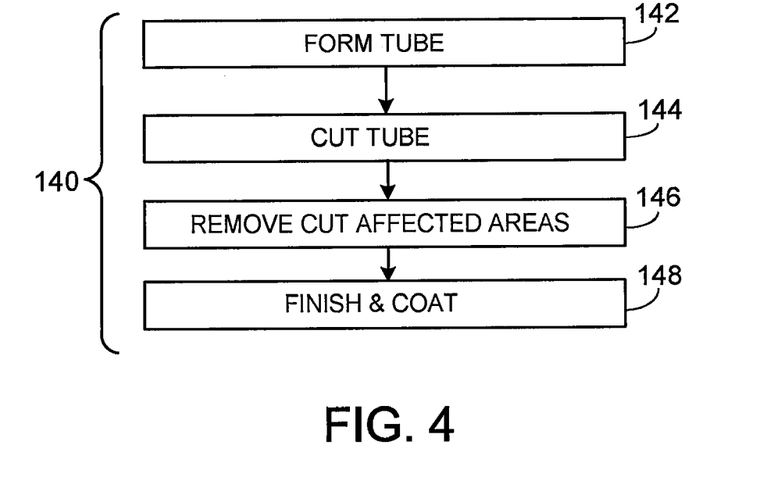
FIG. 4 is a flow chart of an embodiment of a method of making a stent.

FIG. 4 shows a method 140 of making stent 20. As shown, method 140 includes forming a tube (step 142) including composite material 26 that makes up the tubular member of stent 20. The tube is subsequently cut to form bands 22 and connectors 24 (step 144) to produce an unfinished stent. Areas of the unfinished stent affected by the cutting may be subsequently removed (step 146). The unfinished stent may be finished and/or coated to form stent 20 (step 148).

Figure 5:
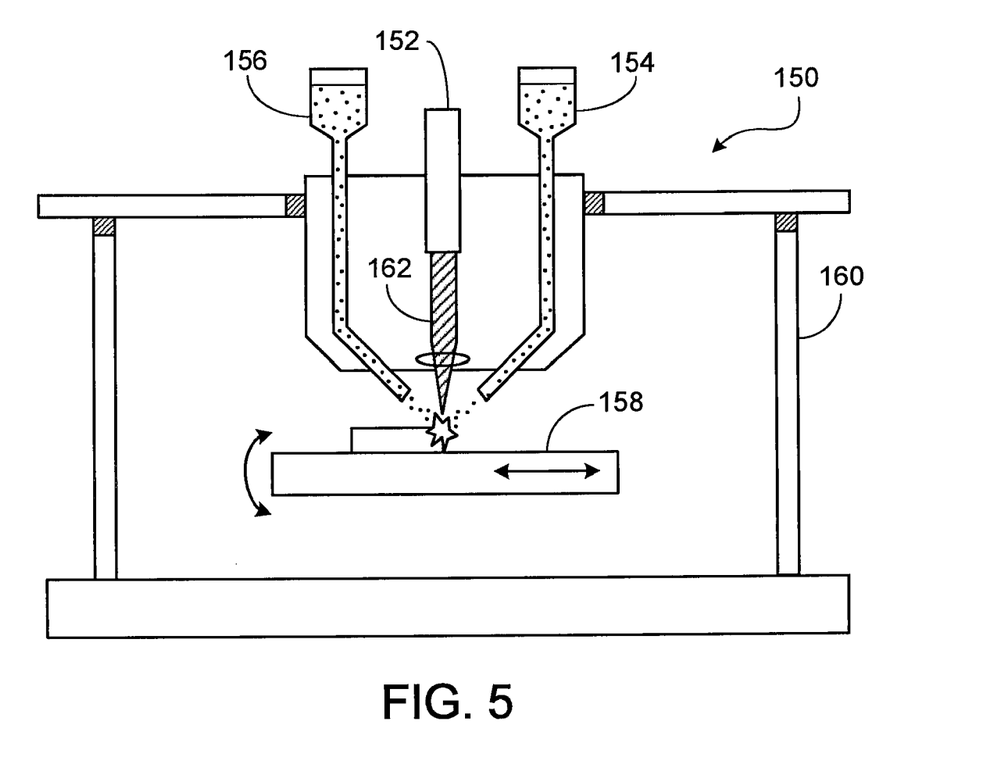
FIG. 5 is a diagrammatic view of an embodiment of a system for making a medical device.

The tube that makes up the tubular member of stent 20 can be formed using metallurgical techniques, such as laser forming. Referring to FIG. 5, a system 150 for making the tubular member is shown. System 150 includes a laser 152, a first hopper 154 containing a material for matrix 28, a second hopper 156 containing a material for particles 30, a movable cylindrical substrate 158, and a chamber 160. Hoppers 154, 156 are configured to selectively deliver their respective materials onto substrate 158. Laser 152 is configured to deliver an energy beam 162 to where the materials from hoppers 154, 156 are delivered on substrate 158. Substrate 158, which is made from a removable material (e.g., carbon steel, cadmium, lead, magnesium, tin, zinc), can be translated and rotated to vary the position on substrate 158 where the materials are deposited and energy beam 162 is addressed. Chamber 160 can be filled and purged with an inert gas to prevent oxidation or contamination of the materials. During fabrication, hoppers 154, 156 deliver their respective material onto substrate 158, and at the same time, laser 152 delivers sufficient energy to melt the matrix material to encapsulate the particles, thereby forming the composite material. To vary the concentrations of the matrix material and/or the particle material, the delivery rate(s) of the hopper(s) can be varied. To vary the compositions or types of particle or matrix materials, additional hoppers containing the desired materials can be used. Substrate 158 is concurrently translated and/or rotated to form a tubular member made of the composite material. In some embodiments, multiple layers of composite material are deposited to form the resulting tubular structure. After the tubular member is made, substrate 158 can be removed by dissolution (e.g., by immersion in an acid such as nitric acid), by mechanical removal (e.g., by grinding), by melting (e.g., for substrate materials having sufficiently low melting points), and/or by sublimation. Laser forming is described, for example, in Stinson et al., U.S. Patent Application Publication No. US 2005/0131522 A1.

Alternatively or additionally, other thermomechanical processes can also be used to form a tubular member made of a composite material. For example, the matrix material need not be molten to form the composite material. The matrix material and the particles can be combined by powder metallurgy techniques (e.g., pressure casting, sintering, hot isostatic pressing, hot working, slurry mixing, direct laser sintering, and/or vacuum plasma deposition, to form a raw material that is subsequently shaped into a feedstock, such as a hollow tubular member. A medical device including a composite material having variable concentrations of particles can be made by joining multiple portions (e.g., billets) of different particle concentrations by sintering. Stents with layers of composite material of different particle concentrations can be formed by sequentially adding the selected composite materials into a mold to form the tubular member.

In some embodiments, the hollow tubular member including the composite material can be drawn through a series of dies with progressively smaller circular openings to plastically deform the member to a targeted size and shape. The plastic deformation strain can harden the member (and increase its yield strength) and elongate the grains along the longitudinal axis of the member. The deformed member can be heat treated (e.g., annealed above the recrystallization temperature and/or hot isostatically pressed) to transform the elongated grain structure into an initial grain structure (e.g., one including equiaxed grains). Small or fine grains can be formed by heating the member close to the recrystallization temperature for a short time. Large or coarse grains can be formed by heating the member at higher temperatures and/or for longer times to promote grain growth.

Next, bands 22 and connectors 24 of stent 20 are formed by cutting the tube (step 144). Selected portions of the tube can be removed to form bands 22 and connectors 24 by laser cutting, as described, for example, in Saunders, U.S. Pat. No. 5,780,807. In certain embodiments, during laser cutting, a liquid carrier, such as a solvent or an oil, is flowed through the lumen of the tube. The carrier can prevent dross formed on one portion of the tube from re-depositing on another portion, and/or can reduce formation of recast material on the tube. Other methods of removing portions of the tube can be used, such as mechanical machining (e.g., micro-machining), electrical discharge machining (EDM), and/or photoetching (e.g., acid photoetching).

In some embodiments, after bands 22 and connectors 24 have been formed, areas of the tube affected by the above-described cutting operation can be removed (step 146). For example, laser machining of bands 22 and connectors 24 can leave a surface layer of melted and resolidified material and/or oxidized metal that can adversely affect the mechanical properties and performance of stent 20. The affected areas can be removed mechanically (e.g., by grit blasting and/or honing) and/or chemically (e.g., by etching and/or electropolishing). In some embodiments, the tubular member can be near-net size configuration after step 146 is performed. "Near-net size" means that the tube has a relatively thin envelope of material that is removed to provide a finished stent. In some embodiments, the tube is formed less than about 25 percent oversized (e.g., less than about 15 percent, 10 percent, or five percent oversized).

The unfinished stent is then finished. Examples of finishing processes include etching (e.g., chemical etching, electrochemical etching) and polishing (e.g., electrolytic polishing, immersion polishing).

In some embodiments, a finishing process can be used to enhance the protrusion of particles 30 from a surface of the stent (e.g., from interior surface 32 and exterior surface 34 of stent body portion 23). As an example, in certain embodiments, an electropolishing process and/or an etching process can be used to enhance the protrusion of particles 30 from a surface of the stent. For example, matrix 28 surrounding particles 30 can be removed such that the particles are undercut, supported by a thin stalk of matrix material. In some embodiments, an electropolishing process can preferentially remove part of matrix 28 (e.g., via dissolution), while not substantially affecting particles 30. For example, particles 30 can be formed of one or more materials (e.g., niobium oxide) that are unlikely to react with the components of the electropolishing bath, while matrix 28 can be formed of one or more materials (e.g., stainless steel) that are likely to dissolve in the electropolishing bath. An electropolishing bath can include, for example, 50 percent sulfuric acid and 50 percent phosphoric acid for stainless steel. The matrix composition and bath parameters such as temperature and agitation can control the amount of the matrix that is removed. In some embodiments, part of matrix 28 that surrounds certain particles 30 can be removed by the electropolishing bath, thereby exposing at least a portion of those particles 30. As a result, those particles 30 can exhibit enhanced protrusion from the surface of the stent. Additionally, an electropolishing process can enhance the smoothness of regions of a surface of a stent that do not include protruding particle In some embodiments, after the stent has been finished, it can undergo cryogenic polishing, for example, typical polishing of refractory material is performed in sulfuric acid and methanol mixtures at −60° C.

After being finished and/or after undergoing cryogenic polishing, the stent can undergo one or more coating processes to form coating 27 and, thereby, stent 20. Coating 27 can be applied to the stent using, for example, one or more dip-coating and/or spraying processes. The protruding particles can mechanically engage (e.g., lock on to) the polymer coating, for example, when the polymer coating surrounds the protruding particles and is locked into place.

Stent 20 can be of a desired shape and size (e.g., coronary stents, aortic stents, peripheral vascular stents, gastrointestinal stents, urology stents, and neurology stents). Depending on the application, stent 20 can have a diameter of between, for example, one millimeter to 46 millimeters. In certain embodiments, a coronary stent can have an expanded diameter of from about two millimeters to about six millimeters. In some embodiments, a peripheral stent can have an expanded diameter of from about five millimeters to about 24 millimeters. In certain embodiments, a gastrointestinal and/or urology stent can have an expanded diameter of from about six millimeters to about 30 millimeters. In some embodiments, a neurology stent can have an expanded diameter of from about one millimeter to about 12 millimeters. An abdominal aortic aneurysm (AAA) stent and a thoracic aortic aneurysm (TAA) stent can have a diameter from about 20 millimeters to about 46 millimeters. Stent 20 can be balloon-expandable, self-expandable, or a combination of both (e.g., Andersen et al., U.S. Pat. No. 5,366,504).

Stent 20 can be delivered and/or expanded using, for example, a catheter delivery system. Catheter systems are described in, for example, Wang, U.S. Pat. No. 5,195,969; Hamlin, U.S. Pat. No. 5,270,086; and Raeder-Devens, U.S. Pat. No. 6,726,712. Stents and stent delivery are also exemplified by the Radius® or Symbiot® systems, available from Boston Scientific Corp., Maple Grove, Minn.

Figure 6A:
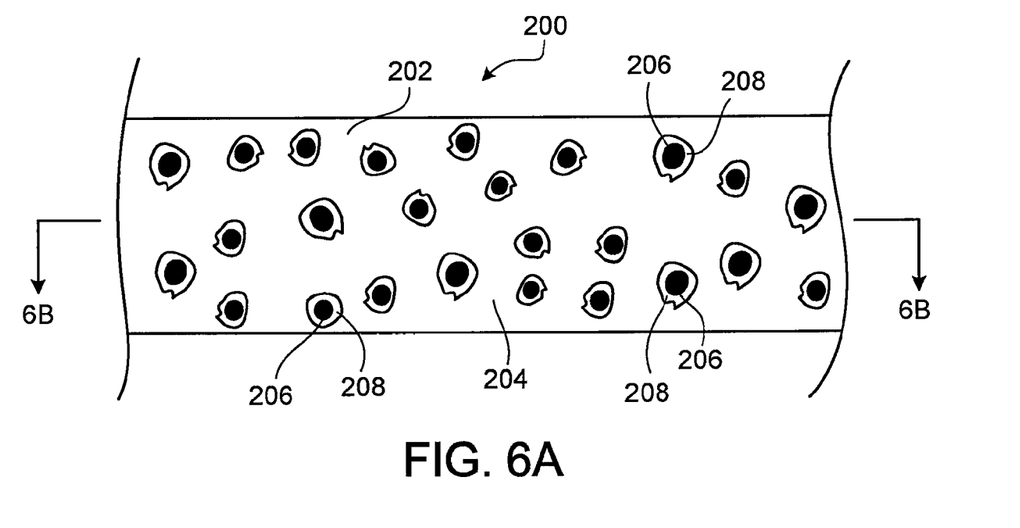
FIG. 6A is a top view of an embodiment of a component of a stent.
Figure 6B:
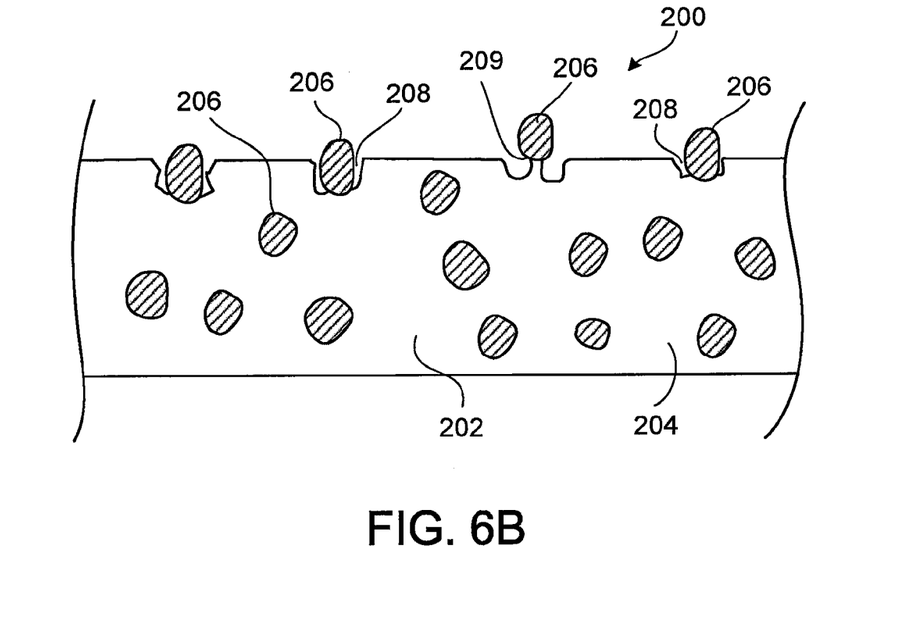
FIG. 6B is a cross-sectional view of the component of FIG. 6A, taken along line 6B-6B.

While stents have been shown including protruding particles, in some embodiments, a stent that includes particles can be treated so that depressions form around the particles. For example, FIGS. 6A and 6B show a portion of a band 200 of a stent. Band 200 is formed of a composite material 202 including a metallic matrix 204 and particles 206. Some of particles 206 are disposed in depressions 208 in matrix 204. Depressions 208 for undercutting 209 can be formed, for example, by subjecting band 200 to a cleaning process, an etching or corrosion process, and/or a polishing process.

In certain embodiments, matrix 204 can be formed of one or more materials that are relatively likely to react with one or more of the materials used during the cleaning, etching or corrosion, and/or polishing processes, while particles 206 can be formed of one or more materials that are relatively unlikely to react with one or more of the materials used during the cleaning, etching or corrosion, and/or polishing processes using acids, bases, fluorides, and/or chelating agents. Thus, the treatment process can cause part of matrix 204 around certain particles 206 to dissolve and/or erode, while not substantially affecting particles 206. This can result in the formation of depressions around certain particles 206. For example, in some embodiments, matrix 204 can be formed of stainless steel, and particles 206 can be formed of silica and/or titania. In some such embodiments, composite material 202 can be treated with an electropolishing process and a crease corrosion solution to form depressions around one or more of the particles. In certain embodiments in which matrix 204 is formed of stainless steel and particles 206 are formed of alumina, composite material 202 can be treated by soaking composite material 202 in a caustic solution and then exposing composite material 202 to a standard electropolishing process. The result can be the formation of depressions around one or more of particles 206.

In certain embodiments, depressions can be formed around particles 206 by dissolving and/or eroding part of particles 206, while not substantially altering matrix 204. For example, a stent including a composite material formed of a steel or titanium matrix and aluminum oxide particles can be exposed to a basic solution (e.g., NaOH, KOH), which can cause part of the aluminum oxide particles to dissolve, thereby resulting in particles surrounded by depressions. While aluminum oxide particles have been described, in some embodiments, the particles can be formed of one or more other materials, such as copper, zinc, calcium, aluminum, nickel, and/or iron.

As the size of a particle 206 increases, the likelihood that a depression will form around the particle during an etching or corrosion process can also increase. Thus, particle sizes can be selected to result in a desired extent of depression formation around some or all of the particles. In some embodiments, a depression can be formed around a particle having a maximum dimension (e.g., a diameter) of at least about one micron. In certain embodiments, a stent including a matrix and particles can be treated (e.g., using an etching or corrosion process) such that certain of the particles erode, dissolve away from, and/or fall out of the stent, thereby resulting in the formation of pores in the stent. In some embodiments, the pores have a small opening to the surface of the stent while having a large internal volume, and can mechanically engage (e.g., lock on to) a polymer coating on the surface of the stent, for example, when a portion of the polymer coating fills the pores during the coating process.

EXAMPLES

The following examples are illustrative and not intended to be limiting.

Example 1

A stent including a particles protruding from its surface can be formed as follows.

A 316L stainless steel can be doped with $NbO_2$ particles using laser forming techniques and subjected to normal stent processing for a 316L stainless steel stent. A tube can be formed using laser forming techniques. The hollow tubular member of the composite material can be drawn through a series of dies with progressively smaller circular openings to plastically deform the member to a targeted size and shape. Next, bands and connectors of the stent can be formed by cutting the tube. The unfinished stent can then be finished by etching (e.g., chemical etching, electrochemical etching) and polishing (e.g., electrolytic polishing, immersion polishing).

Figure 7:
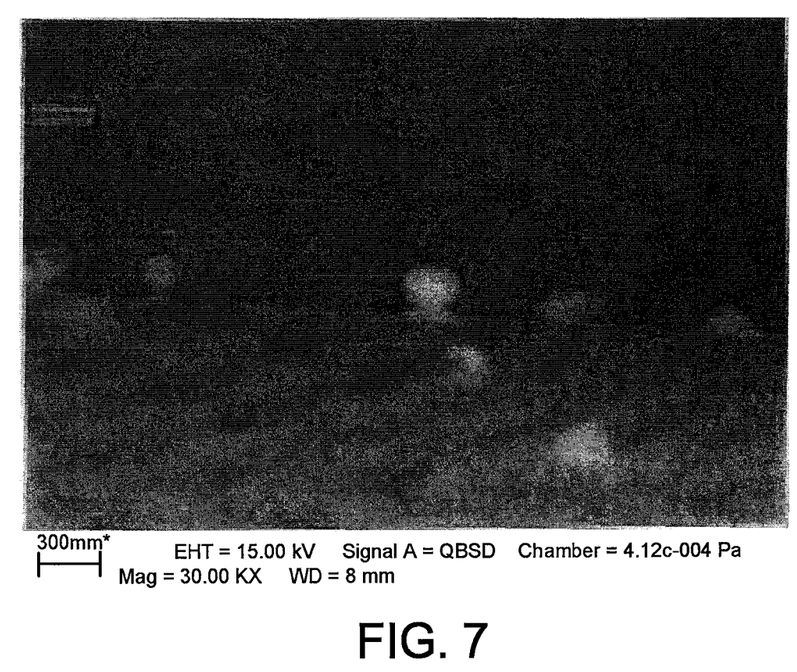
FIG. 7 is a scanning electron micrograph (SEM) image of a surface of a stent, taken at 30,000 times magnification.

FIG. 7 is a scanning electron micrograph (SEM) image of a portion of a surface of the Example 1 stent, taken at 30,000 times magnification. FIG. 7 shows particles protruding from the surface of the stent, resulting in a bulbous, mushroom-like topography on the surface of the stent.

Example 2

A stent including a particles protruding from its surface, with at least one of the particles including a depression formed around it, was formed as follows.

A 316L stainless steel can be doped with $NbO_2$ particles using laser forming techniques and subjected to normal stent processing for a 316L stainless steel stent. A tube can be formed using laser forming techniques. The hollow tubular member of the composite material can be drawn through a series of dies with progressively smaller circular openings to plastically deform the member to a targeted size and shape. Next, bands and connectors of the stent can be formed by cutting the tube. The unfinished stent can then be finished by etching (e.g., chemical etching, electrochemical etching) and polishing (e.g., electrolytic polishing, immersion polishing).

Figure 8:
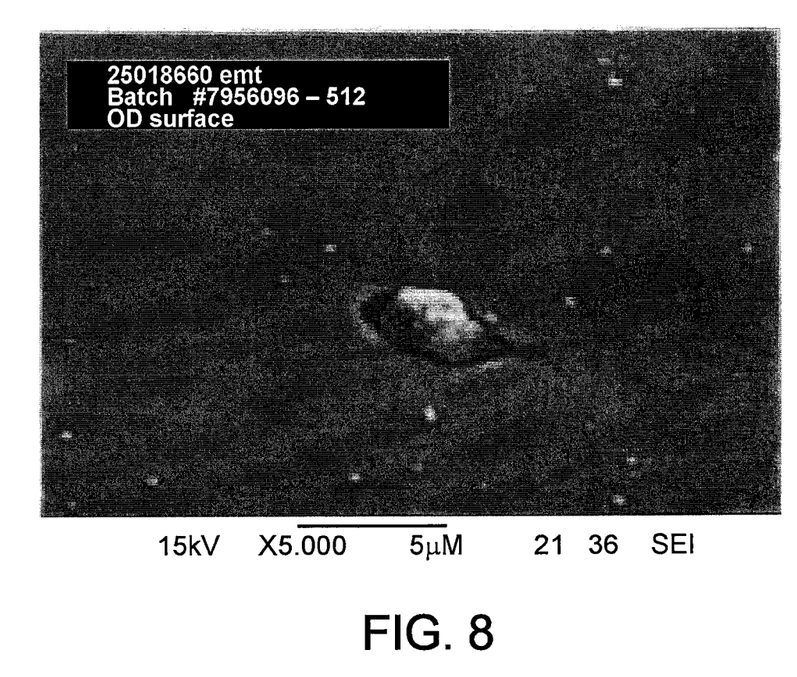
FIG. 8 is an SEM image of a surface of a stent, taken at 5,000 times magnification.

FIG. 8 is a scanning electron micrograph (SEM) image of a portion of a surface of the Example 2 stent, taken at 5,000 times magnification. FIG. 8 shows particles protruding from the surface of the stent, including one relatively large particle with a depression around it.

Other Embodiments

While certain embodiments have been described, other embodiments are possible.

As an example, in some embodiments, a stent can include particles that protrude from a surface of the stent in a pattern. In certain embodiments, the stent can be treated to remove some or all of the protruding particles. This can, for example, result in the formation of a pattern of pores on the surface of the stent. The particles can be removed from the stent by, for example, exposing the stent to one or more oxidizing acidic fluoride-based solutions, such as a solution including nitric acid and ammonium bifluoride (ABF), hydrofluoric acid (HF), or tetrafluoroboric acid ($HBF_4$); a solution including peroxide, sulfuric acid, and ABF, HF, or $HBF_4$; or a solution including peroxide, phosphoric acid, and ABF, HF, or $HBF_4$. While fluoride-based solutions have been described, in some embodiments, particles can be removed from a stent by exposing the stent to one or more chloride-based solutions, such as sulfuric acid-HCl, nitric acid-HCl, and/or phosphoric acid-HCl solution.

In some embodiments, most or all of the particles that protrude from a surface of a stent can be removed to form pores in the stent. The stent can thereafter be treated (e.g., using an electropolishing process that is insensitive to surface chemistry) so that the surface of the stent is relatively smooth.

As an additional example, in some embodiments, one or more annealing cycles can be used on a composite material including particles. The annealing cycles can, for example, make the composite material harder and/or stronger, and/or can affect the uniformity and/or distribution of the particles in the composite material. In certain embodiments, heating the surface of a stent that is formed of a composite material including a metallic matrix and particles can cause the particles at the surface of the stent to join together to form larger particulates, while the particles in the bulk of the stent remain dispersed. The larger particulates can, for example, retain a coating on the stent relatively well (e.g., by interlocking adhesion).

As a further example, in some embodiments, a stent can include one or more therapeutic agents. In certain embodiments, the therapeutic agents can be in the form of one or more coatings on the stent body. In some embodiments, the therapeutic agents can be contained in a coating (e.g., a polymer coating) on the stent body. In some embodiments in which a stent includes depressions and/or pores (e.g., as described above), the depressions and/or pores can contain one or more therapeutic agents. In certain embodiments, the depressions and/or pores can be coated (e.g., to help the depressions and/or pores temporarily retain the therapeutic agents). Examples of therapeutic agents include non-genetic therapeutic agents, genetic therapeutic agents, vectors for delivery of genetic therapeutic agents, cells, and therapeutic agents identified as candidates for vascular treatment regimens, for example, as agents targeting restenosis. Therapeutic agents are described, for example, in Weber, U.S. Patent Application Publication No. US 2005/0261760 A1, published on Nov. 24, 2005, and entitled "Medical Devices and Methods of Making the Same", and in Colen et al., U.S. Patent Application Publication No. US 2005/0192657 A1, published on Sep. 1, 2005, and entitled "Medical Devices". Examples of coating materials that can be used on a stent are described above. Additional examples of coating materials that can be used on a stent include metals (e.g., tantalum, gold, platinum) and metal oxides (e.g., iridium oxide, titanium oxide, tin oxide). Metal and/or metal oxide coatings can be applied to a stent body using, for example, an electroplating process and/or physical vapor deposition (PVD). In some embodiments, a coating on a stent can include one or more bioerodible materials (e.g., sugars, sugar derivatives, and/or salts). Coatings are described, for example, in Colen et al., US Patent Application Publication No. US 2005/0192657 A1.

As another example, while stent 20 is formed entirely of composite material 26, in some embodiments, a composite material can form one or more selected portions of a medical device. For example, a stent can include multiple layers in which one or more layers include a composite material, and one or more layers do not include a composite material. The layer(s) that include a composite material can include the same composite material or different composite materials. The layer(s) that do not include a composite material may include one or more of the biocompatible matrix materials listed above. The layering of the composite material provides yet another way to tailor and tune the properties of the medical device. Stents including multiple layers are described, for example, in Stinson, U.S. Patent Application Publication No. 2004/0044397 A1, and Heath, U.S. Pat. No. 6,287,331.

As a further example, in some embodiments, a stent (e.g., stent 20) can be part of a covered stent or a stent-graft. In certain embodiments, a stent can include and/or be attached to a biocompatible, non-porous or semi-porous polymer matrix made of polytetrafluoroethylene (PTFE), expanded PTFE, polyethylene, urethane, and/or polypropylene.

As an additional example, while certain methods of forming a stent have been described, in some embodiments, one or more other methods can be used to form a stent. For example, in certain embodiments, a stent can be formed by fabricating a wire including a composite material, and knitting and/or weaving the wire into a tubular member.

As a further example, while the addition of particles to a metallic matrix material to form a composite material has been described, in certain embodiments, a composite material including a metallic matrix and inclusions (e.g., oxide inclusions, carbide inclusions) within the matrix can be formed by heating the matrix material. For example, in some embodiments, heat-treating stainless steel can result in the formation of carbide inclusions in the stainless steel. Other methods of forming inclusions in a matrix material include grit blasting the matrix material and chemically or electrochemically oxidizing the surface of a device formed of the matrix material to form metal oxide patches on the surface of the device.

As another example, while stents have been described, the composite materials described herein can be used to form other medical devices. As an example, in some embodiments, a composite material can be used to form other endoprosthesis, such as grafts. As another example, in certain embodiments, a composite material can be used to form a guidewire or a hypotube. A guidewire may have portions including different concentrations of particles to provide a flexible distal section for good trackability and a stiff proximal section for good pushability. As an additional example, in some embodiments, a composite material can be used to form medical implants, such as hip stems and knee trays. As a further example, in certain embodiments, a composite material can be used to form metal staples and wires used for wound closure so that they can be compatible with imaging techniques.

All publications, applications, references, and patents referred to in this application are herein incorporated by reference in their entirety.

Other embodiments are within the claims.

What is claimed is:

1. A medical device, comprising:
   at least one portion comprising:
   a composite material comprising a metallic matrix, and
   a plurality of discrete particles in the matrix, the particles and the matrix having different chemical compositions,
   wherein the at least one portion has a surface and the particles protrude from the surface of the at least one portion, the particles have an average maximum dimension of at least about one micron, and the matrix defines a depression around at least one of the particles protruding from the surface of the at least one portion.

2. The medical device of claim 1, wherein the particles comprise a material selected from the group consisting of metals, oxides, and alloys.

3. The medical device of claim 2, wherein the particles comprise a metal oxide.

4. The medical device of claim 3, wherein the metal oxide is a refractory metal oxide.

5. The medical device of claim 3, wherein the metal oxide is selected from the group consisting of aluminum oxides, niobium oxides, titanium oxides, and chromium oxides.

6. The medical device of claim 1, wherein the particles comprise an oxide selected from the group consisting of silicon oxides, germanium oxides, and gallium oxides.

7. The medical device of claim 1, wherein the particles comprise a metal selected from the group consisting of platinum, palladium, rhodium, iridium, ruthenium, osmium, tungsten, tantalum, titanium, zirconium, hafnium, molybdenum, and gold.

8. The medical device of claim 1, wherein the particles comprise a metal selected from the group consisting of copper, zinc, calcium, aluminum, nickel, and iron.

9. The medical device of claim 1, wherein the particles comprise a material selected from the group consisting of carbides and nitrides.

10. The medical device of claim 1, wherein the composite material comprises at least about 0.5 percent by weight particles.

11. The medical device of claim 10, wherein the composite material comprises at most about two percent by weight particles.

12. The medical device of claim 1, wherein the matrix comprises a material selected from the group consisting of metals and alloys.

13. The medical device of claim 12, wherein the matrix comprises titanium.

14. The medical device of claim 12, wherein the matrix comprises an alloy selected from the group consisting of stainless steel, platinum enhanced radiopaque stainless steel alloys, and cobalt-chromium alloys.

15. The medical device of claim 1, wherein the medical device is an endoprosthesis.

16. The medical device of claim 15, wherein the endoprosthesis is a stent.

17. The medical device of claim 1, further comprising a coating disposed on the surface of the at least one portion.

18. The medical device of claim 17, wherein the coating comprises a polymer.

19. The medical device of claim 1, wherein the particles are elongated fibers.

20. A method, comprising:
    forming a medical device from a composite material comprising a metallic matrix and a plurality of discrete particles in the matrix, the particles and the matrix having different chemical compositions,
    wherein the medical device includes at least one portion having a surface, the particles protrude from the surface of the at least one portion, the particles have an average maximum dimension of at least about one micron, and the matrix defines a depression around at least one of the particles protruding from the surface of the at least one portion.

21. The method of claim 20, further comprising forming a coating on the surface of the at least one portion.

22. The method of claim 20, further comprising treating the medical device to increase the average height of the protrusion of the particles from the surface of the at least one portion.

23. The method of claim 22, wherein treating the medical device comprises electropolishing the medical device.

24. The method of claim 20, further comprising etching the medical device.

25. The method of claim 20, further comprising removing at least one of the particles that protrude from the surface of the at least one portion.

26. The method of claim 20, further comprising removing at least part of the matrix surrounding at least one of the particles protruding from the surface of the at least one portion.

27. The medical device of claim 1, wherein the depression is adapted to contain or temporarily retain one or more therapeutic agents.

28. The medical device of claim 1, wherein the depression around at least one of the particles undercuts at least one of the particles.

* * * * *